United States Patent [19]

Ibe

[11] Patent Number: 4,818,751

[45] Date of Patent: Apr. 4, 1989

[54] COSMETICS

[75] Inventor: Sachiaki Ibe, Tokyo, Japan

[73] Assignee: ZEria Shinyaku Kogyo Kabushiki Kaisha, Tokyo, Japan

[21] Appl. No.: 941,555

[22] Filed: Dec. 11, 1986

Related U.S. Application Data

[63] Continuation of Ser. No. 751,148, Jul. 2, 1985, abandoned.

[51] Int. Cl.$^4$ ............................................. A61K 31/715
[52] U.S. Cl. ..................................... 514/54; 514/844; 514/845; 514/846; 514/847
[58] Field of Search ................. 514/54, 844, 845, 846, 514/847

[56] References Cited

U.S. PATENT DOCUMENTS

| | | | |
|---|---|---|---|
| 3,818,105 | 6/1974 | Coopersmith | 514/845 |
| 4,036,953 | 7/1977 | Adam et al. | 424/92 |
| 4,094,971 | 6/1978 | Chedid et al. | 424/88 |
| 4,123,427 | 10/1978 | Daniel | 424/88 |
| 4,298,494 | 11/1981 | Parslow et al. | 424/70 |
| 4,370,325 | 1/1983 | Packman | 424/70 |
| 4,394,502 | 7/1983 | Maruyama | 424/88 |
| 4,505,900 | 3/1985 | Ribi et al. | 514/2 |
| 4,569,839 | 2/1986 | Grollier et al. | 514/844 |

FOREIGN PATENT DOCUMENTS

| | | | |
|---|---|---|---|
| 53-12428 | 2/1978 | Japan | 514/54 |
| 53-121926 | 10/1978 | Japan | 514/54 |
| 57-146713 | 9/1982 | Japan | 514/54 |

Primary Examiner—Albert T. Meyers
Assistant Examiner—Freda L. Krosnick
Attorney, Agent, or Firm—Scrivener and Clarke

[57] ABSTRACT

The present invention relates to a cosmetic comprising a neutral polysaccharide obtained from an acid-fast bacterium. This cosmetic smoothly spreads on the skin without sticking to the skin to give moistness to the skin. Furthermore, the cosmetic covers the skin and shows an excellent moisture-retaining action, and exerts an effect of preventing or moderating the rough skin.

2 Claims, No Drawings

COSMETICS

This application is a continuation of application Ser. No. 751,148, filed July 2, 1985, now abandoned.

BACKGROUND OF THE INVENTION

The present invention relates to a cosmetic comprising a neutral polysaccharide obtained from acid-fast bacterium.

A polysaccharide is an important biopolymer as well as a nucleic acid, a protein and a lipid, and is utilized in pharmaceutical, food and agricultural chemicals industries and the like. In the field of cosmetics, various polysaccharides have been used as water-soluble high-molecules exerting excellent moisture-retaining or thickening effect. The polysaccharides heretofore used for comsmetics include acidic polysaccharides such as alginic acid, pectin, chondroitin sulfate and hyaluronic acid and neutral polysaccharides such as cellulose, starch, dextran and pullulan. The acidic polysaccharides are defective in that because of ionic characteristic thereof, applicable surfactants are limited and the viscosity is greatly changed with changes in the pH value. The above neutral polysaccharides from natural extracts are defective in that since they ordinarily have a high molecular weight and the distribution range of the molecular weights is wide, the viscosity is high and they do not always give a good feeling during or after use when they are incorporated in cosmetics. Furthermore, neutral polysaccharides become tacky during use or leave a pasty touch after use.

Under the above-mentioned circumstances, the inventor made research with a view to eliminating the above defects and found that a neutral polysaccharide obtained from an acid-fast bacterium has a high water solubilitiy and can exhibit a good moisture-retaining effect to the skin and that its molecular weight is relatively low and the molecular weight distribution range is narrow so that an aqueous solution of this neutral polysaccharide has a low viscosity and can be easily incorporated into a cosmetic base without any great change of the liquid property. It also was found that since this neutral polysaccharide was non-ionic, surfactants could be freely selected and the emulsion stability was good, and that the viscosity were not changed with changes in the pH value. In short, it was found that this neutral polysaccharide has various excellent properties as a cosmetic additive. We have now completed the present invention based on these findings.

DETAILED DESCRIPTION OF THE INVENTION

The acid-fast bacterium used in the present invention belongs to the genus Mycobacterium. Any of bacteria belonging to the genus Mycobacterium may be used, so far as it produces an intended neutral polysaccharide. In view of the mass production and the easiness in culturing, there are preferably used *Mycobacterium tuberculosis, Mycobacterium bovis, Mycobacterium avium, Mycobacterium microti, Mycobacterium phlei* and *Mycobacterium smegmatis*. The culture media which may be used include liquid media such as Sauton medium and glycerol-bouillon medium, and culturing is carried out under ordinary conditions.

The neutral polysaccharide used in the present invention can be obtained by heat-extracting cell body obtained after culturing together with the culture medium or heat-extracting it with water or an alkaline solution directly or, if necessary, after a preliminary treatment such as mechanical or enzymatic disintegration of cell body or defatting with an organic solvent, followed by purification. The composition of the obtained neutral polysaccharide differs to some extent according to the kind of the acid-fast bacterium used, but this difference of the composition has no substantial influences on the properties of a cosmetic in which the neutral polysaccharide is incorporated. The neutral polysaccharide obtained from cells of a bacterium belonging to the genus Mycobacterium is composed mainly of arabinogalactan, arabinomannan, mannan and α-glucan. The cosmetic of the present invention comprises at least one of such neutral polysaccharides having an average molecular weight less than 35,000, and this cosmetic has very excellent characteristics. In order to further specify the present invention, use feelings of the respective components were examined.

If the neutral polysaccharide is incorporated in the cosmetic in an amount of at least 0.0001 (W/W) %, the intended effect is achieved. Although there is no upper limit of the amount added of the neutral polysaccharide, ordinarily it is preferred that the neutral polysaccharide be incorporated in an amount of 0.001 to 2.0(W/W) %, especially 0.01 to 0.2 (W/W) %.

An embodiment of the process for extraction and isolation of the neutral polysaccharide from cell body will now be described.

Cells of *Mycobacterium bovis*, strain BCG are inoculated on the surface of Sauton medium, and culturing is conducted in a thermostat tank maintained at 37° C. until a film-shaped cell body sufficiently forms. Cell body formed on the surface of the culture medium are collected by filtration and the components of the culture medium are washed off by water to obtain wet cells.

The cell body is suspended in a slightly alkaline aqueous solution in an amount 20 times the weight of the wet cell body, and the suspension is heated at 100° C. for 120 minutes to effect extraction. Residual cell body is filtered off using a cell removing filter, and an appropriate amount of sulfosalicylic acid is added to the extract to precipitate proteins. Then, the supernatant is dialyzed with running water. The inner liquid dialysed is concentrated and sodium chloride is added so that the concentration of sodium chloride is 0.9 (W/V) % and then an equal amount of ethanol is added thereto and the mixture is allowed to stand still. The precipitate is removed by centrifugation. Ethanol is added to the supernatant in an amount 4 times that of the supernatant, and the mixture is allowed to stand still, followed by centrifugal separation to collect a crude polysaccharide precipitated.

The collected crude polysaccharide is dissolved in water, and a neutral polysaccharide fraction is obtained by means of ion exchange chromatography. Respective neutral polysaccharides are isolated and purified by ethanol fractionation, gel permeation chromatography, affinity chromatography and the like.

As the result, there are mainly obtained arabinogalactan having an average molecular weight of about 30,000, arabinomannan having an average molecular weight of about 12,000 and mannan having an average molecular weight of about 5,000.

Viscosity and use feelings of simple aqueous solutions formed by dissolving the neutral polysaccharides obtained according to the above procedures and conventional polysaccharides are shown in Table 1.

TABLE 1

Viscosity and Use Feeling of Polysaccharides

| Polysaccharide | Concentration [(W/W) %] | | | | | |
|---|---|---|---|---|---|---|
| | 1 | | 0.1 | | 0.01 | |
| | Viscosity | Use feeling | Viscosity | Use feeling | Viscosity | Use feeling |
| Neutral Polysaccharides of Present Invention | | | | | | |
| arabinogalactan | not changed | B | not changed | A | not changed | A |
| arabinomannan | not changed | B | not changed | A | not changed | A |
| mannan | not changed | B | not changed | A | not changed | A |
| mixture of above three polysaccharides | not changed | B | not changed | A | not changed | A |
| polymeric α-glucan | opacified | C | not changed | B | not changed | A |
| Comparative Polysaccharides | | | | | | |
| pullulan | thickened | D | not changed | D | not changed | C |
| chondroitin sulfate | thickened | D | not changed | D | not changed | C |
| hyaluronic acd | thickened | D | thickened | D | not changed | C |

Note:
A: smooth spreading, no tackiness, fully smooth moisture-retaining feeling after use
B: smooth spreading, no tackiness, moisture-retaining feeling after use
C: smooth spreading with some tackiness, moisture-retaining feeling after use
D: tackiness during use, pasty moisture-retaining feeling after use Each of the neutral polysaccharides used in the present invention, that is, arabinogalactan, arabinomannan and mannan, gives a low viscosity of various concentrations in a broad range and causes no changes in the viscosity. When they are applied on the skin, they smoothly spread without any tackiness and give a good moisture-retaining feeling.

In contrast, each of the conventional polysaccharides and high molecular α-glucan derived from an acid-fast bacterium gives a high viscosity and a tackiness is felt during and after use, and incorporation at a high concentration of 1 to 2 % is difficult.

As is seen from the foregoing, the neutral polysaccharide of the present invention does not change the viscosity at a high concentration of 1 to 2 % and gives an excellent feeling during and after use.

The cosmetic of the present invention does not stick to the skin but smoothly spreads on the skin, and has a good affinity with the skin to give a moist touch to the skin. Furthermore, the cosmetic of the present invention covers the skin to exert a very excellent moisture-retaining action, and an effect of preventing or moderating the rough skin can be attained. These effects can be attained most prominently in case of a facial cosmetic. Of course, the cosmetic of the present invention can also be used as a hair cosmetic or a make-up cosmetic.

As a matter of course, the cosmetic of the present invention may be incorporated with other components in addition to the above-mentioned indispensable component, so far as the qualities and quantities of these components do not inhibit the intended effects of the present invention. They include, for example, animal and vegetable oils and fats such as beef tallow, squalane, olive oil and rice bran oil, mineral oils such as hydrocarbon, liquid paraffin and vaseline, ester oils such as isopropyl myristate, pentaerythritol tetra-2-ethylhexanoate, vitamin A palmitate and vitamin E acetate, silicone oils such as methylphenylsilicone and dimethylsilicone, polyhydric alcohols such as ethylene glycol, propylene glycol, 1,3-butylene glycol, dipropylene glycol, glycerol, polyglycerol, glucose, maltose, maltitol, sorbitol, sucrose and amylolysis sugar, water-soluble high-molecules, water, alcohols such as ethanol and isopropyl alcohol, water-soluble vitamins, antiseptic agents, medicines, surfactants, ultraviolet absorbers, antioxidants, higher fatty acids such as stearic acid and oleic acid, and higher alcohols such as stearyl alcohol, oleyl alcohol and patchouli alcohol.

Examples embodying the present invention will now be described. However, the incorporations of neutral polysaccharides in the present invention are not limited to those shown in the Examples.

EXAMPLE 1

| Softening lotion (weakly acidic) | |
|---|---|
| Moisture-retaining agent: | |
| glycerol | 4.0 (W/W) % |
| 1,3-butylene glycol | 3.0 (W/W) % |
| arabinogalactan | 0.05 (W/W) % |
| Oily component: | |
| 2-decyltetradecanol | 0.1 (W/W) % |
| Solubilizing agent: | |
| polyoxyethylene (20 E.O.) sorbitan monolaurate | 1.5 (W/W) % |
| polyoxyethylene (20 E.O.) lauryl ether | 0.5 (W/W) % |
| Ethanol | 8.0 (W/W) % |
| Perfume | 0.1 (W/W) % |
| Antiseptic agent and ultraviolet absorber | appropriate amounts |
| Purified water | 82.75 (W/W) % |
| preparation process | |

Arabinogalactan, glycerol, 1,3-butylene glycol and the ultraviolet absorber were dissolved in purified water at room temperature. Separately, the oily component, solubilizing agent, antiseptic agent and perfume were dissolved in ethanol at room temperature. The ethanol solution was added to the above purified water solution to effect solubilization, and the mixture was filtered to obtain a softening lotion.

EXAMPLE 2

| Softening lotion (Weakly alkaline) | |
|---|---|
| Moisture-retaining agent: | |
| glycerol | 4.0 (W/W) % |
| 1,3-butylene glycol | 3.0 (W/W) % |
| polyethylene glycol 1500 | 1.0 (W/W) % |
| arabinomannan | 0.05 (W/W) % |
| Solubilizing agent: | |
| polyoxyethylene (15 E.O.) oleyl ether | 2.0 (W/W) % |
| Ethanol | 15.0 (W/W) % |
| Potassium hydroxide | 0.03 (W/W) % |
| Perfume | 0.1 (W/W) % |
| Antiseptic agent and ultraviolet absorber | appropriate amounts |
| Purified water | 74.82 (W/W) % |
| Preparation process | |

Arabinomannan, glycerol, 1,3-butylene glycol, polyethylene glycol 1500 and potassium hydroxide were dissolved in purified water at room temperature. The perfume, antiseptic agent, ultraviolet absorber and polyoxyethylene oleyl ether were dissolved in ethanol at room temperature. The ethanol solution was added to the purified water solution to effect solubilization. The mixture was filtered to obtain a softening lotion.

EXAMPLE 3

| Emollient lotion (o/w non-ionic emulsion) | |
|---|---|
| Oily Component: | |
| squalane | 5.0 (W/W) % |
| Vaseline(registered trademark) | 2.0 (W/W) % |
| beeswax | 0.5 (W/W) % |
| Emulsifier: | |
| sorbitan sesquioleate | 0.8 (W/W) % |
| polyoxyethylene (20 E.O.) oleyl ether | 1.2 (W/W) % |
| Moisture-retaining agent: | |
| 1,3-butylene glycol | 4.0 (W/W) % |
| Mannan | 0.1 (W/W) % |
| Etanol | 5.0 (W/W) % |
| Thickener: | |
| carboxyvinyl polymer (1.0% aqueous solution) | 20.0 (W/W) % |
| Alkali: | |
| Potassium hydroxide | 0.1 (W/W) % |
| Antiseptic agent and antioxidant | appropriate amounts |
| Perfume | 0.5 (W/W) % |
| Purified water | 60.8 (W/W) % |
| Preparation process | |

Mannan and 1,3-butylene glycol were added to purifed water under heating. Ethanol was further added to the mixture and the temperature was adjusted to 70° C. The oleophilic components except the alkali and the aqueous carboxyvinyl polymer solution prepared in advance were mixed under heating and the temperature of the mixture was adjusted to 70° C. This oily phase was added to the above-mentioned aqueous phase and preliminary emulsification was carried out. Then, the aqueous carboxyvinyl polymer solution was added to the mixture and the mixture was homogenized. After neutralizing with alkali, the mixture was homogeneously emulsified by a homogenizing mixer and was cooled to 30° C. by a heat exchanger to obtain an emollient lotion.

EXAMPLE 4

| Emollient lotion (w/o non-ionic emulsion) | |
|---|---|
| Oily component: | |
| microcrystalline wax | 1.0 (W/W) % |
| beeswax | 2.0 (W/W) % |
| lanolin | 2.0 (W/W) % |
| liquid paraffin | 30.0 (W/W) % |
| Emulsifier: | |
| sorbitan sesquioleate | 4.0 (W/W) % |
| polyoxyethylene (20 E.O.) sorbitan monooleate | 1.0 (W/W) % |
| aluminum stearate | 0.2 (W/W) % |
| Moisture-retaining agent: | |
| glycerol | 4.0 (W/W) % |
| α-glucan | 0.1 (W/W) % |
| Perfume | 0.4 (W/W) % |
| Antiseptic agent and antioxidant | appropriate amounts |
| Purified water | 55.3 (W/W) % |
| Preparation process | |

α-Glucan and glycerol were added to the purified water, and the mixture was heated at 70° C. Other components were heated and fused at 70° C. The aqueous phase was gradualy added to this oily phase with stirring, and the mixture was homogeneously emulsified by a homogenizing mixer. The emulsion was cooled to 30° C. by a heat exchanger to obtain an emollient lotion.

EXAMPLE 5

| Emollient cream (non-ionic type) | |
|---|---|
| Oily component: | |
| stearic acid | 2.0 (W/W) % |
| stearyl alcohol | 7.0 (W/W) % |
| reduced lanolin | 2.0 (W/W) % |
| squalane | 5.0 (W/W) % |
| 2-decyltetradecanol | 6.0 (W/W) % |
| Emulsifier: | |
| polyoxyethylene (25 E.O) cetyl ether | 3.0 (W/W) % |
| oleophilic glycerol monostearate | 2.0 (W/W) % |
| Moisture-retaining agent | |
| 1,3-butylene glycol | 4.0 (W/W) % |
| arabinogalactan | 0.075 (W/W) % |
| arabinomannan | 0.075 (W/W) % |
| Perfume | 0.3 (W/W) % |
| Antiseptic agent and antioxidant | appropriate amounts |
| Purified water | 68.55 (W/W) % |
| Preparation process | |

Arabinogalactan, arabinomannan and 1,3-butylene glycol were added to purifed water an the mixture was heated at 70° C. Other components were mixed and heat-fued at 70° C. This oily phase was added to the above aqueous phase, and preliminary emulsification was carried out. The mixture was uniformly emulsified by a homogenizing mixer and cooled to room temperature by a heat exchanger to obtain an emollient cream.

EXAMPLE 6

| Emollient cream (reactive emulsion together with non-ionic surfactant) | |
|---|---|
| Oily component: | |
| beeswax | 2.0 (W/W) % |
| stearyl alcohol | 5.0 (W/W) % |
| stearic acid | 8.0 (W/W) % |
| squalane | 10.0 (W/W) % |
| Emulsifier: | |
| self-emulsifiable propylene glycol monostearate | 3.0 (W/W) % |
| polyoxyethylene (20 E.O) cetyl ether | 1.0 (W/W) % |
| Moisture-retaining agent: | |
| 1,3-butylene glycol | 4.0 (W/W) % |
| glycerol | 4.0 (W/W) % |
| arabinogalactan | 0.05 (W/W) % |
| arabinomannan | 0.05 (W/W) % |
| mannan | 0.05 (W/W) % |
| Alkali: | |
| potassium hydroxide | 0.32 (W/W) % |
| Perfume | 0.5 (W/W) % |
| Antiseptic agent and antioxidant | approprate amounts |
| Purified water | 62.03 (W/W) % |
| Preparation process | |

Arabinogalactan, arabinomannan, mannan, 1,3-butylene glycol, glycerol and potassium hydroxide were added to purified water, and the mixture was heated at 70° C. Other components were mixed and heat-fused at 70° C. This oily phase was added to the above aqueous phase to effect reaction and the reaction mixture was uniformly emulsified by a homogenizing mixer and cooled to 30° C. to obtain an emollient cream.

Comparative Examples 1 and 2

Softening Lotion (weakly acidic)

A softening lotion was prepared in the same manner as described in Example 1 except that arabinogalactan of Example 1 was replaced by purified water (Comparative Example 1) or by pullulan (Comparative Example 2).

Comparative Examples 3 and 4

Softening Lotion (weakly alkaline)

A lotion was prepared in the same manner as described in Example 2 except that arabinomannan of Example 2 was replaced by purified water (Comparative Example 3) or by pullulan (Comparative Example 4).

Comparative Examples 5 and 6

Emollient lotion (o/w non-ionic emulsion)

An emollient lotion was prepared in the same manner as described in Example 3 except that mannan of Example 3 was replaced by purifed water (Comparative Example 5) or by pullulan (Comparative Example 6).

Comparative Examples 7 and 8

Emollient lotion (w/o non-ionic emulsion)

An emollient lotion was prepared in the same manner as described in Example 4 except that α-glucan of Example 4 was replaced by purified water (Comparative Example 7) or by pullulan (Comparative Example 8).

Comparative Examples 9 and 10

Emollient cream (non-ionic type)

An emollient cream was prepared in the same manner as described in Example 5 except that arabinogalactan and arabinomannan of Example 5 were replaced by purified water (Comparative Example 9) or by pullulan (Comparative Example 10).

Comparative Examples 11 and 12

Emollient cream (reactive emulsion together with non-ionic surfactant)

An emollient cream was prepared in the same manner as described in Example 6 except that arabinogalactan, arabinomannan and mannan of Example 6 were replaced by purified water (Comparative Example 11) or by pullulan (Comparative Example 12).

The use feeling test (tackiness, affinity and covering effect during use and tackiness, moistness and moisture-retaining effect after 8 hours) of the cosmetics of the foregoing Examples and Comparative Examples was carried out. The obtained results are shown in Tables 2, 3, 4 and 5.

Test Method

Test time: 9:00 a.m. to 5:00 p.m., 8 hours as a whole

Test conditions: Sample was lightly rubbed into the skin of the face which had been washed with a toilet soap and the skin was lightly massaged.

Panel: 30 women 32 to 48 years old

One of the products of Examples 1 through 6 was applied to the left half face skin and one of the products of Comparative Examples 1, 3, 5, 7, 9 and 11 was applied to the right half face skin, and pair comparison was carried out during use and after 8 hours. In Tables 2 and 3, the number of panelists answering that the indicated products was better is shown. The test was similarly carried out by using the products of Comparative Examples 2, 4, 6, 8, 10 and 12. The obtained results are shown in Tables 4 and 5.

TABLE 2

| Tested Product | Neutral Polysaccharide of Present invention [(W/W) %] | During Use | | |
|---|---|---|---|---|
| | | No tackiness | Affinity | Covering Effect |
| | | (number of panelists) | | |
| Present Invention | | | | |
| Example 1 | 0.05 | 14 | 29 | 28 |
| Example 2 | 0.05 | 18 | 28 | 24 |
| Example 3 | 0.10 | 13 | 29 | 30 |
| Example 4 | 0.10 | 17 | 29 | 30 |
| Example 5 | 0.15 | 15 | 30 | 30 |
| Example 6 | 0.15 | 14 | 30 | 29 |
| Comparison | | | | |
| Comparative Example 1 | 0 | 16 | 1 | 2 |
| Comparative Example 3 | 0 | 12 | 2 | 6 |
| Comparative Example 5 | 0 | 17 | 1 | 0 |

TABLE 2-continued

| Tested Product | Neutral Polysaccharide of Present invention [(W/W) %] | During Use | | |
|---|---|---|---|---|
| | | No tackiness | Affinity | Covering Effect |
| | | (number of panelists) | | |
| Comparative Example 7 | 0 | 13 | 1 | 0 |
| Comparative Example 9 | 0 | 15 | 0 | 0 |
| Comparative Example 11 | 0 | 16 | 0 | 1 |

As is apparent from the foregoing results, the products of Examples 1 through 6 according to the present invention are not different from those of Comparative Examples 1, 3, 5, 7, 9 and 11 free of a neutral polysaccharide in the tackiness during use, and the former products are prominently excellent over the latter products in the affinity with the skin and the covering effect.

TABLE 3

| Tested Product | Neutral Polysaccharide of Present invention [(W/W) %] | 8 Hours after Use | | |
|---|---|---|---|---|
| | | No tackiness | Moistness | Moisture-retaining Effect |
| | | (number of panelists) | | |
| Present Invention | | | | |
| Example 1 | 0.05 | 15 | 29 | 30 |
| Example 2 | 0.05 | 17 | 29 | 30 |
| Example 3 | 0.10 | 18 | 28 | 27 |
| Example 4 | 0.10 | 17 | 27 | 27 |
| Example 5 | 0.15 | 14 | 30 | 30 |
| Example 6 | 0.15 | 14 | 30 | 30 |
| Comparison | | | | |
| Comparative Example 1 | 0 | 15 | 1 | 0 |
| Comparative Example 3 | 0 | 13 | 1 | 0 |
| Comparative Example 5 | 0 | 12 | 2 | 3 |
| Comparative Example 7 | 0 | 13 | 3 | 3 |
| Comparative Example 9 | 0 | 16 | 0 | 0 |
| Comparative Example 11 | 0 | 16 | 0 | 0 |

As is apparent from the foregoing results, the products of Examples 1 through 6 according to the present invention are not different from those of Comparative Examples 1, 3, 5, 7, 9 and 11 free of a neutral polysaccharide in the tackiness 8 hours after use, and the former products are prominently excellent over the latter products in the moistness and the moisture-retaining effect.

TABLE 4

| Tested Product | Neutral Polysaccharide | During Use | | |
|---|---|---|---|---|
| | | No tackiness | Affinity | Covering Effect |
| | | (number of panelists) | | |
| Present Invention | Neutral polysaccharide of Present Invention [(W/W) %] | | | |
| Example 1 | 0.05 | 30 | 28 | 28 |
| Example 2 | 0.05 | 30 | 28 | 28 |
| Example 3 | 0.10 | 29 | 24 | 26 |
| Example 4 | 0.10 | 30 | 27 | 27 |
| Example 5 | 0.15 | 30 | 29 | 30 |
| Example 6 | 0.15 | 30 | 30 | 30 |
| Comparison | Pullulan [(W/W) %] | | | |
| Comparative Example 2 | 0.05 | 0 | 2 | 2 |
| Comparative Example 4 | 0.05 | 0 | 2 | 2 |
| Comparative Example 6 | 0.10 | 1 | 6 | 4 |
| Comparative Example 8 | 0.10 | 0 | 3 | 3 |
| Comparative Example 10 | 0.15 | 6 | 1 | 0 |
| Comparative Example 12 | 0.15 | 0 | 0 | 0 |

As is apparent from the foregoing results, the products of Examples 1 through 6 containing the neutral polysaccharide of the present invention are prominently excellent over those of Comparative Examples 2, 4, 6, 8, 10 and 12 containing pullulan in the same amount in the tackiness, the affinity with the skin and the covering effect during use.

TABLE 5

| Tested Product | Neutral Polysaccharide | 8 Hours after Use | | |
| --- | --- | --- | --- | --- |
| | | No tackiness | Moistness | Moisture-retaining Effect |
| | | (number of panelists) | | |
| Present Invention | Neutral polysaccharide of Present Invention [(W/W) %] | | | |
| Example 1 | 0.05 | 30 | 29 | 29 |
| Example 2 | 0.05 | 30 | 29 | 30 |
| Example 3 | 0.10 | 30 | 27 | 29 |
| Example 4 | 0.10 | 30 | 26 | 30 |
| Example 5 | 0.15 | 30 | 29 | 30 |
| Example 6 | 0.15 | 30 | 30 | 30 |
| Comparison | Pullulan [(W/W) %] | | | |
| Comparative Example 2 | 0.05 | 0 | 1 | 1 |
| Comparative Example 4 | 0.05 | 0 | 1 | 0 |
| Comparative Example 6 | 0.10 | 0 | 3 | 1 |
| Comparative Example 8 | 0.10 | 0 | 4 | 0 |
| Comparative Example 10 | 0.15 | 0 | 1 | 0 |
| Comparative Example 12 | 0.15 | 0 | 0 | 0 |

As is apparent from the foregoing results, the products of Examples 1 through 6 containing the neutral polysaccharide of the present invention are prominently excellent over those of Comparative Examples 2, 4, 6, 8, 10 and 12 containing pullulan in the same amount in the tackiness, the moistness and the moisture-retaining effect 8 hours after use.

What is claimed is:

1. A cosmetic preparation for topical skin application comprising:
   (1) 55.3–82.75 (W/W)% of water as a primary vehicle;
   (2) at least one skin treating component selected from the group consisting of:
      (a). 4–8 (W/W)% of polyhydric alcohol moisture-retaining agents, and
      (b). 0.1–35 (W/W)% of oily component;
   (3) and about 0.01–about 0.2 (W/W)% of at least one of a neutral polysaccharide selected from the group consisting of arabinogalactan having an average molecular weight of about 30,000, arabinomannan having an average molecular weight of about 12,000, and mannan having an average molecular weight of about 5,000 wherein said polysaccharide is obtained from cells of a bacterium from the genus Mycobacterium, and causes no change in viscosity of the cosmetic preparation.

2. A cosmetic preparation as set forth in claim 1, wherein said Mycobacterium is selected from the group consisting of *Mycobacterium tuberculosis, Mycobacterium bovis, Mycobacterium avium, Mycobacterium microti, Mycobacterium phlei,* and *Mycobacterium smegmatis.*

* * * * *